United States Patent
Webb et al.

(10) Patent No.: US 10,004,593 B2
(45) Date of Patent: Jun. 26, 2018

(54) INTRAOCULAR LENS WITH ELASTIC MASK

(71) Applicant: AcuFocus, Inc., Irvine, CA (US)

(72) Inventors: R. Kyle Webb, Carlsbad, CA (US); Daniel David Siems, Aliso Viejo, CA (US); Adam C. Reboul, Sarasota, FL (US); Patrick H. Benz, Sarasota, FL (US); Bruce Arthur Christie, Claremont, CA (US)

(73) Assignee: AcuFocus, Inc., Irvine, CA (US)

( * ) Notice: Subject to any disclaimer, the term of this patent is extended or adjusted under 35 U.S.C. 154(b) by 0 days. days.

(21) Appl. No.: 14/454,585

(22) Filed: Aug. 7, 2014

(65) Prior Publication Data

US 2015/0073549 A1    Mar. 12, 2015

Related U.S. Application Data

(63) Continuation-in-part of application No. 12/856,492, filed on Aug. 13, 2010, now Pat. No. 9,492,272.
(Continued)

(51) Int. Cl.
*A61F 2/16* (2006.01)
*B29D 11/00* (2006.01)
(Continued)

(52) U.S. Cl.
CPC .......... *A61F 2/1613* (2013.01); *A61F 2/1659* (2013.01); *B29C 39/026* (2013.01);
(Continued)

(58) Field of Classification Search
CPC .... A61F 2/1613; A61F 2/1659; A61F 2/1648; A61F 2230/0065; A61F 2250/0018; A61F 2250/004; A61F 2250/0053; A61F 2250/0091; B29D 11/00048; B29D 11/00442
(Continued)

(56) References Cited

U.S. PATENT DOCUMENTS 2,350,421 A    6/1944 Schoder et al.
2,470,927 A    5/1949 Hale, Jr.
(Continued)

FOREIGN PATENT DOCUMENTS

AU    2004201751    5/2004
CN    1875895    12/2006
(Continued)

OTHER PUBLICATIONS

International Search Report and Written Opinion for PCT/US2014/050223 dated Nov. 27, 2014 in 14 pages.
(Continued)

*Primary Examiner* — Paul Prebilic
(74) *Attorney, Agent, or Firm* — Knobbe Martens Olson & Bear LLP

(57) ABSTRACT

Intraocular implants and methods of making intraocular implants are provided. The intraocular implant can include a lens body having a lens material and a mask having a mask material. The lens body can be secured to the mask. The mask material can include a modulus of elasticity that is greater than or equal to a modulus of elasticity of the lens material.

12 Claims, 5 Drawing Sheets

Related U.S. Application Data

(60) Provisional application No. 61/233,804, filed on Aug. 13, 2009, provisional application No. 61/233,794, filed on Aug. 13, 2009, provisional application No. 61/863,833, filed on Aug. 8, 2013.

(51) Int. Cl.
| | |
|---|---|
| *B29C 39/10* | (2006.01) |
| *B29C 39/02* | (2006.01) |
| *B29K 101/12* | (2006.01) |
| *B29K 701/12* | (2006.01) |
| *B29L 11/00* | (2006.01) |
| *B29L 31/00* | (2006.01) |

(52) U.S. Cl.
CPC ........ *B29C 39/10* (2013.01); *B29D 11/00048* (2013.01); *B29D 11/00442* (2013.01); *A61F 2210/0076* (2013.01); *A61F 2250/0018* (2013.01); *A61F 2250/0053* (2013.01); *A61F 2250/0098* (2013.01); *B29K 2101/12* (2013.01); *B29K 2701/12* (2013.01); *B29K 2715/00* (2013.01); *B29K 2995/0012* (2013.01); *B29K 2995/0046* (2013.01); *B29L 2011/0016* (2013.01); *B29L 2031/7532* (2013.01)

(58) Field of Classification Search
USPC ........................................................ 623/6.17
See application file for complete search history.

(56) References Cited

U.S. PATENT DOCUMENTS

| | | |
|---|---|---|
| 3,034,403 A | 5/1962 | Neefe |
| 3,270,099 A | 8/1966 | Camp |
| 3,458,870 A | 8/1969 | Stone |
| 3,578,850 A | 5/1971 | Grant |
| 3,776,230 A | 12/1973 | Neefe |
| 3,794,414 A | 2/1974 | Wesley |
| 3,877,502 A | 4/1975 | Hunckler |
| 3,996,627 A | 12/1976 | Deeg et al. |
| 4,010,496 A | 3/1977 | Neefe |
| 4,104,338 A | 8/1978 | Guerrieri |
| 4,116,439 A | 9/1978 | Chavarria et al. |
| 4,210,391 A | 7/1980 | Cohen |
| 4,298,996 A | 11/1981 | Barnet |
| 4,340,283 A | 7/1982 | Cohen |
| 4,402,579 A | 9/1983 | Poler |
| 4,423,728 A | 1/1984 | Lieberman |
| 4,435,050 A | 3/1984 | Poler |
| 4,450,593 A | 5/1984 | Poler |
| 4,505,855 A | 3/1985 | Bruns et al. |
| 4,563,565 A | 1/1986 | Kampfer et al. |
| 4,575,373 A | 3/1986 | Johnson |
| 4,607,617 A | 8/1986 | Choyce |
| 4,624,669 A | 11/1986 | Grendahl |
| 4,639,105 A | 1/1987 | Neefe |
| 4,646,720 A | 3/1987 | Peyman et al. |
| 4,655,774 A | 4/1987 | Choyce |
| 4,665,913 A | 5/1987 | Esperance, Jr. |
| 4,669,466 A | 6/1987 | L'Esperance |
| 4,669,834 A | 6/1987 | Richter |
| 4,676,790 A | 6/1987 | Kern |
| 4,676,791 A | 6/1987 | LeMaster et al. |
| 4,678,422 A | 7/1987 | York |
| 4,701,038 A | 10/1987 | Neefe |
| 4,715,858 A | 12/1987 | Lindstrom |
| 4,767,647 A | 8/1988 | Bree |
| 4,795,462 A | 1/1989 | Grendahl |
| 4,798,608 A | 1/1989 | Grendahl |
| 4,799,784 A | 1/1989 | Safir |
| 4,799,931 A | 1/1989 | Lindstrom |
| 4,807,623 A | 2/1989 | Lieberman |
| 4,813,955 A | 3/1989 | Achatz et al. |
| 4,815,690 A | 3/1989 | Shepherd |
| 4,817,789 A | 4/1989 | Paul |
| 4,842,599 A | 6/1989 | Bronstein |
| 4,851,003 A | 7/1989 | Lindstrom |
| 4,863,466 A | 9/1989 | Schlegel |
| 4,881,860 A | 11/1989 | Kanazawa |
| 4,903,695 A | 2/1990 | Warner et al. |
| 4,907,586 A | 3/1990 | Bille et al. |
| 4,928,815 A | 5/1990 | Paul |
| 4,955,904 A | 9/1990 | Atebara et al. |
| 4,976,732 A | 12/1990 | Vorosmarthy |
| 4,994,080 A | 2/1991 | Shepard |
| 5,013,319 A | 5/1991 | Davis |
| 5,030,230 A | 7/1991 | White |
| 5,041,133 A | 8/1991 | Sayano et al. |
| 5,055,602 A | 10/1991 | Melpolder |
| 5,087,015 A | 2/1992 | Galley |
| 5,090,955 A | 2/1992 | Simon |
| 5,094,521 A | 3/1992 | Jolson et al. |
| 5,098,443 A | 3/1992 | Parel et al. |
| 5,112,328 A | 5/1992 | Taboada et al. |
| 5,120,120 A | 6/1992 | Cohen |
| 5,120,121 A | 6/1992 | Rawlings et al. |
| 5,137,441 A | 8/1992 | Fogarty |
| 5,147,395 A | 9/1992 | Willis |
| 5,171,318 A | 12/1992 | Gibson et al. |
| 5,185,107 A | 2/1993 | Blake |
| 5,188,494 A | 2/1993 | Hatin |
| 5,192,316 A | 3/1993 | Ting |
| 5,196,026 A | 3/1993 | Barrett et al. |
| 5,213,749 A | 5/1993 | Huss et al. |
| 5,260,727 A | 11/1993 | Oksman et al. |
| 5,266,241 A | 11/1993 | Parekh |
| 5,269,795 A | 12/1993 | Arnott |
| 5,269,812 A | 12/1993 | White |
| 5,274,404 A | 12/1993 | Michael |
| 5,288,436 A | 2/1994 | Liu et al. |
| 5,292,514 A | 3/1994 | Capecchi et al. |
| 5,300,116 A | 4/1994 | Chirila et al. |
| 5,312,330 A | 5/1994 | Klopotek |
| 5,314,439 A | 5/1994 | Sugita |
| 5,314,961 A | 5/1994 | Anton et al. |
| 5,332,802 A | 7/1994 | Kelman et al. |
| 5,336,261 A | 8/1994 | Barrett et al. |
| 5,354,331 A | 10/1994 | Schachar et al. |
| 5,358,520 A | 10/1994 | Patel |
| 5,372,580 A | 12/1994 | Simon et al. |
| 5,391,201 A | 2/1995 | Barrett et al. |
| 5,441,511 A | 8/1995 | Hanna |
| 5,474,548 A | 12/1995 | Knopp et al. |
| 5,507,740 A | 4/1996 | O'Donnell, Jr. |
| 5,547,468 A | 8/1996 | Simon et al. |
| D375,245 S | 11/1996 | Irving |
| 5,578,080 A | 11/1996 | McDonald |
| 5,603,774 A * | 2/1997 | LeBoeuf ............ A61F 2/1613 134/1 |
| 5,607,437 A | 3/1997 | Simon et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,647,865 A | 7/1997 | Swinger |
| 5,653,752 A | 8/1997 | Silvestrini et al. |
| 5,662,706 A | 9/1997 | Legerton et al. |
| 5,693,268 A | 12/1997 | Widman et al. |
| 5,697,923 A | 12/1997 | Poler |
| 5,702,440 A | 12/1997 | Portney |
| 5,708,049 A | 1/1998 | Katagiri et al. |
| 5,713,957 A | 2/1998 | Steele et al. |
| 5,722,971 A | 3/1998 | Peyman |
| 5,725,575 A | 3/1998 | O'Donnell, Jr. |
| 5,746,558 A | 5/1998 | Nygren et al. |
| 5,752,967 A | 5/1998 | Kritzinger et al. |
| 5,769,889 A | 6/1998 | Kelman |
| 5,774,202 A | 6/1998 | Abraham et al. |
| 5,824,086 A | 10/1998 | Silvestrini |
| 5,837,156 A | 11/1998 | Cumming |
| 5,843,105 A | 12/1998 | Mathis et al. |

(56) References Cited

U.S. PATENT DOCUMENTS

| | | | |
|---|---|---|---|
| 5,864,128 A | 1/1999 | Plesko | |
| 5,870,167 A | 2/1999 | Knopp et al. | |
| 5,895,610 A | 4/1999 | Chang et al. | |
| 5,905,561 A | 5/1999 | Lee et al. | |
| 5,910,537 A | 6/1999 | Feingold et al. | |
| 5,913,898 A | 6/1999 | Feingold et al. | |
| 5,919,185 A | 7/1999 | Peyman | |
| 5,925,294 A | 7/1999 | Shibuya | |
| 5,964,748 A | 10/1999 | Peyman | |
| 5,964,776 A | 10/1999 | Peyman | |
| 5,965,330 A | 10/1999 | Evans et al. | |
| 5,980,040 A | 11/1999 | Xu et al. | |
| 6,017,121 A | 1/2000 | Chateau et al. | |
| 6,063,073 A | 5/2000 | Peyman | |
| 6,090,141 A | 7/2000 | Lindstrom | |
| 6,102,946 A | 8/2000 | Nigam | |
| 6,106,553 A | 8/2000 | Feingold et al. | |
| 6,110,166 A | 8/2000 | Juhasz et al. | |
| 6,138,307 A | 10/2000 | McDonald | |
| 6,152,959 A | 11/2000 | Portney | |
| 6,164,777 A | 12/2000 | Li et al. | |
| 6,171,336 B1 | 1/2001 | Sawusch | |
| 6,178,593 B1 | 1/2001 | Carlson | |
| 6,197,019 B1 | 3/2001 | Peyman | |
| 6,201,036 B1 | 3/2001 | Fedorov et al. | |
| 6,203,538 B1 | 3/2001 | Peyman | |
| 6,210,401 B1 | 4/2001 | Lai | |
| 6,217,571 B1 | 4/2001 | Peyman | |
| 6,217,596 B1 | 4/2001 | Farah | |
| 6,221,067 B1 | 4/2001 | Peyman | |
| 6,228,113 B1 | 5/2001 | Kaufman | |
| 6,228,114 B1 | 5/2001 | Lee | |
| 6,228,115 B1 | 5/2001 | Hoffmann et al. | |
| 6,264,648 B1 | 7/2001 | Peyman | |
| 6,277,146 B1 * | 8/2001 | Peyman | A61F 2/1613 623/6.17 |
| 6,280,470 B1 | 8/2001 | Peyman | |
| 6,280,471 B1 | 8/2001 | Peyman et al. | |
| 6,302,877 B1 | 10/2001 | Ruiz | |
| 6,304,390 B1 | 10/2001 | Takanashi | |
| 6,308,590 B1 | 10/2001 | Berto | |
| 6,316,153 B1 | 11/2001 | Goodman et al. | |
| 6,335,190 B1 | 1/2002 | Zhou et al. | |
| 6,361,560 B1 | 3/2002 | Nigam | |
| 6,387,379 B1 | 5/2002 | Goldberg et al. | |
| 6,391,230 B1 | 5/2002 | Sarbadhikari | |
| 6,416,179 B1 | 7/2002 | Lieberman et al. | |
| 6,423,093 B1 | 7/2002 | Hicks et al. | |
| 6,432,246 B1 | 8/2002 | Blake | |
| 6,436,092 B1 | 8/2002 | Peyman | |
| 6,458,141 B1 | 10/2002 | Peyman | |
| 6,461,384 B1 | 10/2002 | Hoffmann et al. | |
| 6,491,637 B2 | 12/2002 | Foster et al. | |
| 6,497,700 B1 | 12/2002 | LaHaye | |
| 6,515,006 B2 | 2/2003 | Horn | |
| 6,551,307 B2 | 4/2003 | Peyman | |
| 6,554,424 B1 | 4/2003 | Miller et al. | |
| 6,554,860 B2 | 4/2003 | Hoffmann et al. | |
| 6,555,103 B2 | 4/2003 | Leukel et al. | |
| 6,575,573 B2 | 6/2003 | Lai et al. | |
| 6,581,993 B2 | 6/2003 | Nigam | |
| 6,588,902 B2 | 7/2003 | Isogai | |
| 6,589,280 B1 | 7/2003 | Koziol | |
| 6,607,527 B1 | 8/2003 | Ruiz et al. | |
| 6,613,088 B1 | 9/2003 | Babizhayev | |
| 6,638,304 B2 | 10/2003 | Azar | |
| 6,649,722 B2 | 11/2003 | Rosenzweig et al. | |
| 6,655,804 B2 | 12/2003 | Streibig | |
| 6,692,126 B1 | 2/2004 | Xie et al. | |
| 6,702,807 B2 | 3/2004 | Peyman | |
| 6,726,322 B2 | 4/2004 | Andino et al. | |
| 6,740,116 B2 | 5/2004 | Morcher | |
| 6,755,858 B1 | 6/2004 | White | |
| 6,786,926 B2 | 9/2004 | Peyman | |
| 6,811,256 B1 | 11/2004 | Becherer et al. | |
| 6,855,163 B2 | 2/2005 | Peyman | |
| 6,874,886 B2 | 4/2005 | Miller et al. | |
| 6,899,424 B2 | 5/2005 | Miller et al. | |
| 6,949,093 B1 | 9/2005 | Peyman | |
| 6,951,556 B2 | 10/2005 | Epstein | |
| 6,966,648 B2 | 11/2005 | Miller et al. | |
| 6,989,008 B2 | 1/2006 | Peyman | |
| 6,997,428 B1 | 2/2006 | Andino et al. | |
| 7,001,374 B2 | 2/2006 | Peyman | |
| 7,008,447 B2 | 3/2006 | Koziol | |
| 7,025,455 B2 | 4/2006 | Roffman | |
| 7,061,693 B2 * | 6/2006 | Zalevsky | A61F 2/16 359/559 |
| 7,099,057 B2 | 8/2006 | Parker et al. | |
| 7,276,080 B2 | 10/2007 | Murakami et al. | |
| 7,287,852 B2 | 10/2007 | Fiala | |
| 7,364,674 B1 | 4/2008 | Hoover | |
| 7,399,811 B2 | 7/2008 | Mentak et al. | |
| 7,404,637 B2 | 7/2008 | Miller et al. | |
| 7,404,638 B2 | 7/2008 | Miller et al. | |
| 7,446,157 B2 | 11/2008 | Mentak et al. | |
| 7,455,404 B2 | 11/2008 | Bandhauer et al. | |
| 7,455,691 B2 | 11/2008 | Feingold et al. | |
| 7,477,452 B2 | 1/2009 | Tsuruma | |
| 7,491,350 B2 | 2/2009 | Silvestrini | |
| 7,497,866 B2 | 3/2009 | Perez | |
| 7,628,810 B2 | 12/2009 | Christie et al. | |
| 7,641,337 B2 | 1/2010 | Altmann | |
| 7,645,299 B2 | 1/2010 | Koziol | |
| 7,745,555 B2 | 6/2010 | Mentak et al. | |
| 7,842,367 B2 | 11/2010 | Mentak | |
| 7,976,577 B2 | 7/2011 | Silvestrini | |
| D645,337 S | 9/2011 | Hsu et al. | |
| 8,043,371 B2 | 10/2011 | Paul et al. | |
| 8,048,972 B2 | 11/2011 | Mentak et al. | |
| 8,079,706 B2 | 12/2011 | Silvestrini et al. | |
| D656,526 S | 3/2012 | Christie et al. | |
| 8,241,354 B2 | 8/2012 | Hong et al. | |
| 8,287,592 B2 | 10/2012 | Silvestrini | |
| 8,343,215 B2 | 1/2013 | Miller et al. | |
| 8,349,006 B2 | 1/2013 | Zhao et al. | |
| D681,086 S | 4/2013 | Christie et al. | |
| 8,420,753 B2 | 4/2013 | Mentak et al. | |
| 8,460,374 B2 | 6/2013 | Christie et al. | |
| 8,568,478 B2 | 10/2013 | Zickler et al. | |
| 8,604,098 B2 | 12/2013 | Boydston et al. | |
| 8,740,978 B2 | 6/2014 | Weeber et al. | |
| 8,752,958 B2 | 6/2014 | Miller et al. | |
| 8,858,624 B2 | 10/2014 | Christie et al. | |
| 8,864,824 B2 | 10/2014 | Silvestrini et al. | |
| 9,005,281 B2 | 4/2015 | Christie et al. | |
| 9,138,142 B2 | 9/2015 | Christie et al. | |
| 9,204,962 B2 | 12/2015 | Silvestrini | |
| 9,427,311 B2 * | 8/2016 | Christie | G02C 7/165 |
| 9,427,922 B2 | 8/2016 | Reboul et al. | |
| 9,492,272 B2 * | 11/2016 | Christie | A61F 2/1613 |
| 9,545,303 B2 * | 1/2017 | Vilupuru | A61B 3/102 |
| 9,573,328 B2 | 2/2017 | Reboul et al. | |
| 9,603,704 B2 | 3/2017 | Silvestrini | |
| 9,757,227 B2 | 9/2017 | Kushlin et al. | |
| 2001/0027314 A1 | 10/2001 | Peyman | |
| 2001/0034516 A1 | 10/2001 | Peyman | |
| 2001/0050750 A1 | 12/2001 | Breger | |
| 2002/0010510 A1 | 1/2002 | Silvestrini | |
| 2002/0082288 A1 | 6/2002 | Horn | |
| 2002/0120329 A1 | 8/2002 | Lang et al. | |
| 2002/0167640 A1 | 11/2002 | Francis et al. | |
| 2002/0196409 A1 | 12/2002 | Jani | |
| 2003/0014042 A1 | 1/2003 | Juhasz et al. | |
| 2003/0105521 A1 | 6/2003 | Perez | |
| 2003/0135272 A1 | 7/2003 | Brady et al. | |
| 2003/0149480 A1 | 8/2003 | Shadduck | |
| 2003/0204258 A1 | 10/2003 | Graham et al. | |
| 2003/0216763 A1 | 11/2003 | Patel | |
| 2004/0019379 A1 | 1/2004 | Glick et al. | |
| 2004/0056371 A1 | 3/2004 | Liao et al. | |
| 2004/0068317 A1 | 4/2004 | Knight | |
| 2004/0106929 A1 | 6/2004 | Masket | |
| 2004/0140578 A1 | 7/2004 | Kelly et al. | |

(56) References Cited

U.S. PATENT DOCUMENTS

| | | |
|---|---|---|
| 2005/0027355 A1 | 2/2005 | Murakami et al. |
| 2005/0046794 A1 | 3/2005 | Silvestrini et al. |
| 2005/0056954 A1 | 3/2005 | Devlin |
| 2005/0090895 A1 | 4/2005 | Peyman |
| 2005/0124983 A1 | 6/2005 | Frey et al. |
| 2005/0137703 A1 | 6/2005 | Chen |
| 2005/0143751 A1* | 6/2005 | Makker .................. G02B 1/043 606/107 |
| 2005/0143812 A1* | 6/2005 | Paul ...................... A61F 2/1613 623/6.3 |
| 2005/0182488 A1 | 8/2005 | Peyman |
| 2005/0187621 A1 | 8/2005 | Brady |
| 2005/0288784 A1 | 12/2005 | Peyman |
| 2006/0064077 A1 | 3/2006 | Peyman |
| 2006/0079959 A1 | 4/2006 | Christie et al. |
| 2006/0079960 A1* | 4/2006 | Christie ................. A61B 3/152 623/5.11 |
| 2006/0113054 A1 | 6/2006 | Silvestrini |
| 2006/0184243 A1 | 8/2006 | Yilmaz |
| 2006/0232665 A1 | 10/2006 | Schowengerdt et al. |
| 2006/0235428 A1 | 10/2006 | Silvestrini |
| 2006/0235514 A1 | 10/2006 | Silvestrini |
| 2006/0241751 A1 | 10/2006 | Marmo et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271177 A1 | 11/2006 | Christie et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0032866 A1 | 2/2007 | Portney |
| 2007/0091472 A1* | 4/2007 | Alkemper ................ G02B 3/00 359/796 |
| 2007/0092592 A1 | 4/2007 | Chiang |
| 2007/0129797 A1 | 6/2007 | Lang et al. |
| 2007/0225691 A1 | 9/2007 | Silvestrini et al. |
| 2008/0033546 A1 | 2/2008 | Liang |
| 2008/0077238 A1 | 3/2008 | Deacon et al. |
| 2008/0100921 A1 | 5/2008 | Nishikawa |
| 2008/0151183 A1 | 6/2008 | Altmann |
| 2008/0208335 A1 | 8/2008 | Blum et al. |
| 2008/0212030 A1 | 9/2008 | Bentley et al. |
| 2008/0220214 A1 | 9/2008 | Uozu et al. |
| 2008/0221674 A1 | 9/2008 | Blum et al. |
| 2008/0255663 A1 | 10/2008 | Akpek et al. |
| 2008/0269884 A1* | 10/2008 | Vannoy .................. A61F 2/1613 623/6.17 |
| 2008/0306587 A1 | 12/2008 | Your |
| 2009/0012505 A1 | 1/2009 | Chernyak |
| 2009/0021692 A1 | 1/2009 | Miller et al. |
| 2009/0059168 A1 | 3/2009 | Miller et al. |
| 2009/0069817 A1 | 3/2009 | Peyman |
| 2009/0171458 A1 | 7/2009 | Kellan et al. |
| 2009/0204207 A1 | 8/2009 | Blum et al. |
| 2009/0222086 A1 | 9/2009 | Lui et al. |
| 2009/0234448 A1* | 9/2009 | Weeber .................. A61F 2/1613 623/6.3 |
| 2009/0287306 A1* | 11/2009 | Smith ..................... A61F 2/1627 623/5.16 |
| 2009/0306773 A1 | 12/2009 | Silverstrini et al. |
| 2010/0082100 A1* | 4/2010 | Mikawa .................. A61F 2/1613 623/6.17 |
| 2010/0127412 A1 | 5/2010 | Lake |
| 2010/0149618 A1* | 6/2010 | Sprague ............. G02B 27/0172 359/259 |
| 2010/0312336 A1 | 12/2010 | Hong et al. |
| 2011/0037184 A1* | 2/2011 | Shoji ...................... A61L 27/00 264/1.36 |
| 2011/0040376 A1 | 2/2011 | Christie et al. |
| 2011/0125261 A1 | 5/2011 | Portney |
| 2011/0166652 A1 | 7/2011 | Bogaert et al. |
| 2011/0172675 A1 | 7/2011 | Danta et al. |
| 2011/0251685 A1 | 10/2011 | Chu |
| 2012/0109294 A1 | 5/2012 | Olson |
| 2012/0143325 A1 | 6/2012 | Christie et al. |
| 2012/0203239 A1 | 8/2012 | Vukich et al. |
| 2012/0245683 A1 | 9/2012 | Christie et al. |
| 2012/0310338 A1 | 12/2012 | Christie et al. |
| 2013/0053953 A1 | 2/2013 | Silvestrini |
| 2013/0103147 A1 | 4/2013 | Christie et al. |
| 2013/0131795 A1 | 5/2013 | Miller et al. |
| 2013/0238091 A1 | 9/2013 | Danta et al. |
| 2013/0268071 A1* | 10/2013 | Vilupuru ................ A61B 3/102 623/6.17 |
| 2014/0131905 A1 | 5/2014 | Webb |
| 2014/0264981 A1 | 9/2014 | Reboul et al. |
| 2014/0277432 A1 | 9/2014 | Silvestrini |
| 2014/0379078 A1 | 12/2014 | Trindade |
| 2015/0025627 A1 | 1/2015 | Christie et al. |
| 2015/0177422 A1 | 6/2015 | Liu et al. |
| 2015/0183173 A1 | 7/2015 | Linhardt et al. |
| 2015/0366658 A1 | 12/2015 | Christie et al. |
| 2016/0081794 A1 | 3/2016 | Silvestrini |
| 2016/0135947 A1 | 5/2016 | Webb et al. |
| 2016/0229134 A1* | 8/2016 | Reboul .............. B29D 11/0048 |
| 2017/0143477 A1* | 5/2017 | Christie ................ A61F 2/1613 |
| 2017/0144392 A1 | 5/2017 | Reboul et al. |
| 2017/0189167 A1 | 7/2017 | Vilupuru et al. |

FOREIGN PATENT DOCUMENTS

| | | |
|---|---|---|
| CN | 101322663 | 12/2008 |
| DE | 4134320 | 4/1992 |
| EP | 0165652 | 12/1985 |
| EP | 0443094 | 8/1991 |
| EP | 1173790 | 1/2002 |
| EP | 1674049 | 6/2006 |
| EP | 1548489 B1 | 8/2006 |
| EP | 2319457 | 5/2011 |
| EP | 2243052 B1 | 9/2011 |
| EP | 2365379 | 9/2011 |
| EP | 2455799 | 5/2012 |
| EP | 2823789 | 1/2015 |
| EP | 2364457 B1 | 8/2015 |
| FR | 2620687 | 3/1989 |
| FR | 2649605 | 1/1991 |
| GB | 1276003 | 6/1972 |
| JP | 62-167343 | 7/1987 |
| JP | 64-002644 | 1/1989 |
| JP | H02-7954 | 1/1990 |
| JP | 04-158859 | 6/1992 |
| JP | 06-509731 | 3/1993 |
| JP | H05-65340 | 9/1993 |
| JP | 06-502782 | 3/1994 |
| JP | H07-067896 | 3/1995 |
| JP | 07-265340 | 10/1995 |
| JP | 08-103457 A | 4/1996 |
| JP | H09-502542 | 3/1997 |
| JP | 11-503657 | 8/1997 |
| JP | 07-178125 | 7/1998 |
| JP | 2000-047145 | 2/2000 |
| JP | 2002-537895 | 11/2002 |
| JP | 2003-502109 | 1/2003 |
| JP | 2004-510199 | 4/2004 |
| JP | 2004-538034 | 12/2004 |
| JP | 2005-533576 | 11/2005 |
| JP | 2007-516794 | 6/2007 |
| JP | 2007-523720 | 8/2007 |
| JP | 2008-506710 | 3/2008 |
| JP | S59-54527 | 5/2008 |
| KR | 10-0335722 | 5/2002 |
| RU | 2138837 | 9/1999 |

(56) References Cited

FOREIGN PATENT DOCUMENTS

| | | |
|---|---|---|
| SU | 1380743 A1 | 3/1988 |
| WO | WO 87/05797 | 10/1987 |
| WO | WO 95/03747 | 2/1995 |
| WO | WO 95/08135 | 3/1995 |
| WO | WO 96/35397 | 11/1996 |
| WO | WO 98/48715 | 11/1998 |
| WO | WO 00/25704 | 5/2000 |
| WO | WO 00/38594 | 7/2000 |
| WO | WO 00/51682 | 9/2000 |
| WO | WO 00/52516 | 9/2000 |
| WO | WO 00/70388 | 11/2000 |
| WO | WO 01/10641 | 2/2001 |
| WO | WO 01/15779 | 3/2001 |
| WO | WO 01/17460 | 3/2001 |
| WO | WO 01/19364 | 3/2001 |
| WO | WO 01/82815 | 11/2001 |
| WO | WO 02/076320 | 10/2002 |
| WO | WO 02/102241 | 12/2002 |
| WO | WO 03/020177 | 3/2003 |
| WO | WO 03/022168 | 3/2003 |
| WO | WO 03/061518 | 7/2003 |
| WO | WO 2004/014969 | 2/2004 |
| WO | WO 2004/034917 | 4/2004 |
| WO | WO 2004/105588 | 12/2004 |
| WO | WO 2004/113959 | 12/2004 |
| WO | WO 2005/082265 | 9/2005 |
| WO | WO 2006/020638 | 2/2006 |
| WO | WO 2006/047534 | 5/2006 |
| WO | WO 2006/060380 | 6/2006 |
| WO | WO 2006/113377 | 10/2006 |
| WO | WO 2006/113411 | 10/2006 |
| WO | WO 2006/113563 | 10/2006 |
| WO | WO 2006/113564 | 10/2006 |
| WO | WO 2007/057734 | 10/2007 |
| WO | WO 2007/133384 | 11/2007 |
| WO | WO 2007/142981 | 12/2007 |
| WO | WO 2008/036671 | 3/2008 |
| WO | WO 2008/102096 | 8/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/059214 | 5/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2012/170066 | 12/2012 |
| WO | WO 2013/019871 | 2/2013 |
| WO | WO 2013/082545 | 6/2013 |
| WO | WO 2013/101793 | 7/2013 |
| WO | WO 2013/112589 | 8/2013 |
| WO | WO 2013/123265 | 8/2013 |
| WO | WO 2014/054946 | 4/2014 |
| WO | WO 2014/074610 | 5/2014 |
| WO | WO 2014/158653 | 10/2014 |
| WO | WO 2015/021323 | 2/2015 |
| WO | WO 2015/069927 | 5/2015 |
| WO | WO 2015/073718 | 5/2015 |
| WO | WO 2016/081493 | 5/2016 |
| WO | WO 2017/062316 | 4/2017 |
| WO | WO 2017/091520 | 6/2017 |

OTHER PUBLICATIONS

Lu Xuequan, et al. "Radiation preparation and thermo-response swelling of interpenetrating polymer network hydrogel composed of PNIPAAm and PMMA", Radiation Physics and Chemistry, vol. 57, Mar. 2000, pp. 477-480, XP002473596.

Aniridia Implants. (Aug. 24, 2011). Retrieved Feb. 5, 2015, from https://web.archive.org/web/20110824062840/http://www.morcher.com/nc/produkte/aniridiaimplants.html.

Patel, C.K., et al. "Imaging the macula through a black occlusive intraocular lens". Arch. Ophthalmol. Oct. 2010; 128(10):1374-1376.

Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-513.

Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.

Guyton A.C., Textbook of Medical Physiology, 7th Edition, W.B. Saunders Company, Jan. 1986: Chapter 58, pp. 700-710.

* cited by examiner

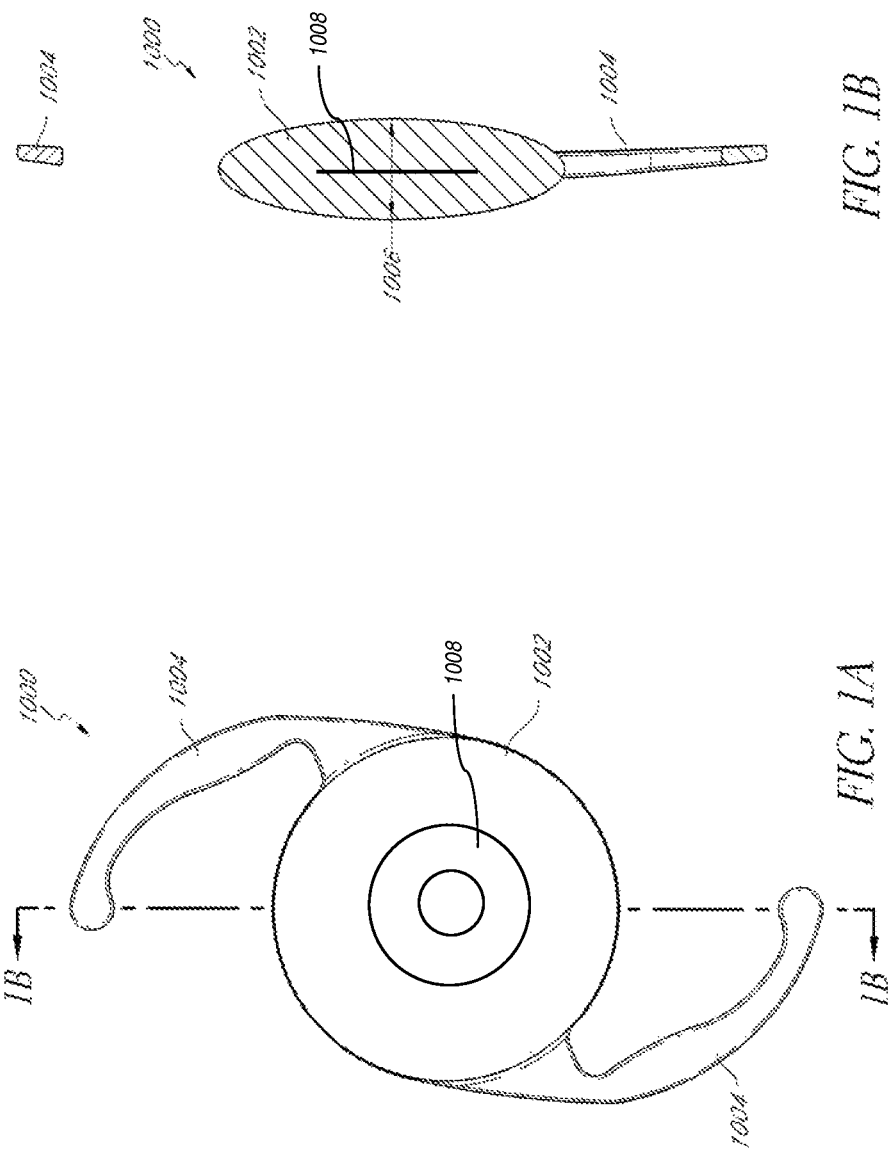

INTRAOCULAR LENS WITH ELASTIC MASK

INCORPORATION BY REFERENCE TO ANY PRIORITY APPLICATIONS

This application is a continuation-in-part of U.S. application Ser. No. 12/856,492, filed Aug. 13, 2010, titled "MASKED INTRAOCULAR IMPLANTS AND LENSES," now U.S. Pat. No. 9,492,272 which claims priority benefit under 35 U.S.C. § 119(e) of U.S. Provisional Application No. 61/233,804, filed Aug. 13, 2009, titled "MASKED INTRAOCULAR IMPLANTS AND LENSES," and U.S. Provisional Application No. 61/233,794, filed Aug. 13, 2009, titled "INTRAOCULAR IMPLANT WITH PRESBYOPIC CORRECTION," each of which is hereby incorporated by reference in its entirety. This application also claims priority benefit under 35 U.S.C. § 119(e) of U.S. Provisional Application No. 61/863,833, filed Aug. 8, 2013, titled "INTRAOCULAR LENS WITH ELASTIC MASK," which is hereby incorporated by reference in its entirety.

BACKGROUND

Field

This application relates generally to the field of intraocular devices. More particularly, this application is directed to intraocular implants and lenses (IOLs) with an aperture to increase depth of focus (e.g. "masked" intraocular lenses), and methods of making the same.

Description of the Related Art

The human eye functions to provide vision by transmitting and focusing light through a clear outer portion called the cornea, and further refining the focus of the image onto a retina by way of a crystalline lens. The quality of the focused image depends on many factors including the size and shape of the eye, and the transparency of the cornea and the lens.

The optical power of the eye is determined by the optical power of the cornea and the crystalline lens. In a normal, healthy eye, sharp images of distant objects are formed on the retina (emmetropia). In many eyes, images of distant objects are either formed in front of the retina because the eye is abnormally long or the cornea is abnormally steep (myopia), or formed in back of the retina because the eye is abnormally short or the cornea is abnormally flat (hyperopia). The cornea also may be asymmetric or toric, resulting in an uncompensated cylindrical refractive error referred to as corneal astigmatism.

Some people suffer from cataracts in which the crystalline lens undergoes a loss of transparency. In such cases, the crystalline lens can be removed and replaced with an intraocular lens (IOL). However, some intraocular lenses may still leave defects in a patient's non-distance eyesight.

SUMMARY

Certain aspects of this disclosure are directed toward an intraocular lens including a mask embedded within, or secured to, a lens body including a lens material. The mask can include an aperture for improving depth of focus. Further, the mask can include a mask material having a modulus of elasticity that is within about 30 percent of a modulus of elasticity of the lens material.

Certain aspects of this disclosure are directed toward an intraocular lens including a mask embedded within, or secured to, a lens body including a lens material. The mask can include an aperture for improving depth of focus. Further, the mask can include a mask material having a coefficient of thermal expansion that is within about 30 percent of the coefficient of thermal expansion of the lens material. In some embodiments, the mask material has a coefficient of thermal expansion that is within about 20 percent, within about 10 percent, or within about 5 percent of the coefficient of thermal expansion of the lens material.

In any of the above mentioned aspects, the intraocular lens can be configured such that a pre-injection optical power of the intraocular lens can be within about 0.5 diopters, preferably within about 0.3 diopters, or within about 0.2 diopters, or within about 0.1 diopters, of a post-injection optical power of the intraocular lens.

In any of the above mentioned aspects, the modulus of elasticity of the mask material can be within about 20 percent of the modulus of elasticity of the lens material, or within about 10 percent of the modulus of elasticity of the lens material, or within about 5 percent greater than the modulus of elasticity of the lens material. In some embodiments, the modulus of elasticity of the mask material can be greater than or equal to the modulus of elasticity of the lens material. In some embodiments, the modulus of elasticity of the mask material can be less than the modulus of elasticity of the lens material.

In any of the above mentioned aspects, the mask material can include silicone or acrylic.

In any of the above mentioned aspects, the lens material and the mask material can include the same material.

In any of the above mentioned aspects, the mask can include a plurality of holes characterized in that at least one of a hole size, shape, orientation, and spacing of the plurality of holes is varied to reduce the tendency of the holes to produce visible diffraction patterns.

In any of the above mentioned aspects, the mask can include a thickness of less than or equal to about 200 microns, preferably less than or equal to about 100 microns. For example, the thickness can be at least about 4 microns and less than or equal to about 20 microns, or less than or equal to about 15 microns, or less than or equal to about 10 microns.

In any of the above mentioned aspects, the lens body can include an outer diameter between about 3 mm and about 6 mm. Further, the lens body can be capable of insertion through an incision having a chord length of less than or equal to about 3.0 mm or less than or equal to about 2.4 mm.

In any of the above mentioned aspects, the intraocular lens can be configured such that a room temperature optical power of the intraocular lens can be within about 0.15 diopters, such as within about 0.03 diopters of 0.1 diopters, for example, about 0.13 diopters, of a body temperature optical power of the intraocular lens.

In any of the above mentioned aspects, the intraocular lens can undergo a temperature differential of about 10° C. without substantially affecting optical power.

Certain aspects of this disclosure are directed toward a method of implanting an intraocular lens. The method can include creating an incision having a chord length of less than or equal to about 2.4 mm, and injecting an intraocular lens through the incision using an injector system.

The injected intraocular lens can include a mask embedded within, or secured to, a lens body including a lens material. The mask can include an aperture for improving depth of focus. In some embodiments, the modulus of elasticity of the mask material can be within about 30 percent of the modulus of elasticity of the lens material, or within about 20 percent of the modulus of elasticity of the lens material, or within about 10 percent of the modulus of elasticity of the lens material, or within about 5 percent of the modulus of elasticity of the lens material. In some embodiments, the modulus of elasticity of the mask material can be greater than or equal to the modulus of elasticity of the lens material. In some embodiments, the modulus of elasticity of the mask material can be less than the modulus of elasticity of the lens material. The intraocular lens can further include any of the aspects of the intraocular lenses described above.

Certain aspects of this disclosure are directed toward a method of implanting an intraocular lens. The method can include creating an incision, injecting an intraocular lens through the incision using an injector system, and introducing the intraocular lens to a temperature differential of at least about 10° C. without substantially affecting optical power.

The injected intraocular lens can include a mask embedded within, or secured to, a lens body including a lens material. The mask can include an aperture for improving depth of focus. Further, the mask can include a material having a coefficient of thermal expansion that is within about 30 percent of a coefficient of thermal expansion of the lens material, within about 20 percent of a coefficient of thermal expansion of the lens material, within about 10 percent of a coefficient of thermal expansion of the lens material, or within about 5 percent of a coefficient of thermal expansion of the lens material. The intraocular lens can further include any of the aspects of the intraocular lenses described above.

Certain aspects of this disclosure are directed toward a method of manufacturing an intraocular lens. The method can include forming a mask with an aperture for improving depth of focus from a mask material, inserting a lens material into a mold, and curing the lens material to form a lens body. The lens body can include the mask therein. The lens material can include a modulus of elasticity that is within about 30 percent of a modulus of elasticity of the mask material. The intraocular lens can further include any of the aspects of the intraocular lenses described above.

Certain aspects of this disclosure are directed toward a method of manufacturing an intraocular lens. The method can include forming a mask with an aperture for improving depth of focus from a mask material, inserting a lens material into a mold, and curing the lens material to form a lens body. The lens body can include the mask therein. Further, the lens material can include a coefficient of thermal expansion that is within about 30 percent of a coefficient of thermal expansion of the mask material. The intraocular lens can further include any of the aspects of the intraocular lenses described above.

In any of the above mentioned methods of manufacturing, the method can include forming the mask by spin-casting the mask material, stamping the mask material, printing the mask material, or extruding the mask material.

In any of the above mentioned methods of manufacturing, the method can include, after curing the lens material, chemically extracting residual lens material.

Any feature, structure, or step disclosed herein can be replaced with or combined with any other feature, structure, or step disclosed herein, or omitted. Further, for purposes of summarizing the disclosure, certain aspects, advantages and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 1A illustrates a top view of an example embodiment of an intraocular lens having an embedded mask for improving depth of focus.

FIG. 1B illustrates a cross-sectional view of the intraocular lens of FIG. 1A taken along line 1B-1B.

DETAILED DESCRIPTION

Figure 2A:
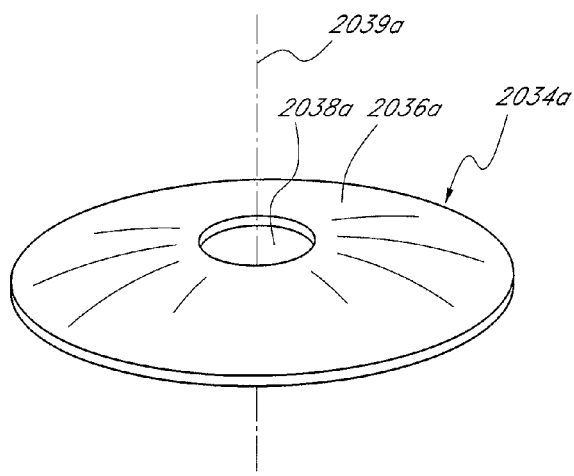
FIG. 2A is a perspective view of one embodiment of a mask configured to increase depth of focus.

As discussed herein, people who undergo intraocular lens (IOL) implantation surgery may still suffer from defects in their non-distance eyesight (e.g., presbyopia). One technique for treating such defects is by including a mask within the IOL that increases the patient's depth of focus. The intraocular implants of the embodiments described herein include a mask adapted to provide a small aperture for light to pass through to the retina to increase depth of focus. The light rays that pass through the mask within the IOL converge at substantially a single focal point on the retina, while the light rays that would not converge at the single point on the retina are blocked by the mask.

Several alternatives to fixed-focus IOLs have been developed for improving non-distance eyesight, including multifocal IOLs and accommodating IOLs. These devices attempt to provide the ability to see clearly at both near and far distances. However, accommodating IOLs can be complex and some multifocal IOLs do not perform well at intermediate distances and cause glare, halos, and night vision difficulties associated with the presence of unfocused light. This limitation can force designers of multifocal optics to choose how much of the light is directed to each focal point, and to deal with the effects of the unfocused light that is always present in any image. In order to maximize acuity at the important distances of infinity (e.g., >6 M) and 40 cm (e.g., a normal reading distance), it is typical to provide little or no light focused at an intermediate distance, and as a result, visual acuity at these distances is poor. With a mask that includes an aperture to increase depth-of-focus, however, the intermediate vision of a patient can be improved significantly. For example, the defocus blur associated with the aperture can be less at intermediate distances than at near.

FIGS. 1A-B illustrate an example embodiment of an intraocular lens having an embedded mask 1008 for increasing depth of focus. The intraocular lens 1000 can include haptics 1004 for positioning the lens within the eye. The cross-sectional thickness of the lens body 1002 is generally dependent on the optical power of the intraocular lens 1000 and the material of the lens body 1002. In particular, the central region of the lens body 1002 is generally the thickest section of the intraocular lens 1000 with a central region cross-sectional thickness 1006. Methods for reducing the thickness of the intraocular lens are described in U.S. Pub. No. 2011/0040376, filed Aug. 13, 2010, which is incorporated herein by reference in its entirety. Any of the teachings of this prior publication can also be applied to the devices and methods in the present disclosure.

One method of implanting the IOL 1000 can include inserting the IOL through a small incision in the eye. The IOL 1000 can be inserted into the eye using an injector system. The injector system can include a cartridge tip for housing the IOL 1000. The size of the hole in the cartridge tip through which the IOL 1000 is injected is typically smaller than the size of the IOL. Thus, the IOL 1000 is deformed (e.g., stretched) when passing through the tip during the injection process. The IOL 1000 can be made of a resilient material such that it can revert back to its pre-injection shape after passing through the cartridge tip. When using this method, the size of the incision is generally dependent on the size of the cartridge tip. Typically, smaller surgical incisions are associated with better surgical outcomes.

However, the size of the cartridge tip and incision can be limited by the material properties of the lens body. This problem can be further complicated by the embedded mask 1008 within the IOL 1000. For example, as the IOL 1000 is pushed through the cartridge tip, the extrusion forces can not only stretch or otherwise deform the IOL but also the embedded mask 1008. In addition, the location of the embedded mask 1008 within the IOL 1000 can be displaced (e.g., the embedded mask can become transversely de-centered and/or longitudinally biased to either side of the desired longitudinal depth of the embedded mask within the IOL).

After releasing the IOL 1000 from the cartridge tip, it is desirable that the IOL 1000 and the embedded mask 1008 achieve a target post-injection optical performance specification (e.g., optical power, presbyopia correction, etc.). For example, it may be desirable for the post-injection optical performance to substantially match the pre-injection optical performance. Thus, in some embodiments, the IOL 1000 and the embedded mask 1008 have material properties (e.g., elasticity) that allow them to revert back to their pre-injection shapes, and, in the case of the embedded mask, its pre-injection location within the IOL.

Similar issues are pertinent to the method of manufacturing the IOL 1000 with the embedded mask 1008. IOL manufacturing processes can involve steps where the IOL swells, undergoes temperature differentials, etc. The mask can be deformed if it does not have sufficient elasticity or a compatible coefficient of thermal expansion when compared to the IOL material.

Some methods of manufacturing the IOL 1000 can include chemically extracting impurities from the IOL. For example, the chemical extraction process can be used to remove residual lens material monomer. The chemical extraction process can include immersing the IOL in a chemical (e.g., hexane, benzene, or alcohol) over a pre-determined period of time and a particular temperature profile. In some instances, during the chemical extraction process, the lens body can undergo a volumetric increase of at least about 10%. If the material properties of the mask material differ too much from the material properties of the lens material, then the mask 1008 can undergo deformation and/or displacement, thus degrading the optical performance of the IOL. This can occur if, for example, the modulus of elasticity of the mask material is much different than the modulus of elasticity of the lens material.

It can be particularly difficult to maintain the desired optical performance through deformations and temperature differentials when the mask 1008 and the lens body exhibit incompatible material properties (e.g. modulus of elasticity or coefficient of thermal expansion). If one or both of the mask material and lens body material do not exhibit appropriate material properties, the mask 1008 and/or lens body can be permanently deformed or, in the case of the embedded mask, biased to an undesired location within the IOL, during deformations (such as those that may occur during chemical extractions), and/or temperature shifts. This can affect optical performance (e.g., optical power or presbyopia correction). For example, if the lens body exhibits greater elasticity than the mask material, then, after injection, the mask 1008 can be deformed and degrade the optical performance of the IOL 1000. As another example, if the coefficients of expansion of the lens material and the mask material are too different, when the IOL transitions from room temperature (e.g., about 20° C.) to body temperature (e.g., about 35-37° C.), the resulting stress and strain can cause the mask to be deformed and degrade the optical performance of the IOL.

Provided below are examples of IOLs with embedded masks that are designed to overcome the issues described above. In some implementations, the IOLs (e.g., 1000) with embedded masks (e.g., 1008) that are described herein include substantially the same optical characteristics pre-injection and post-injection.

Masks

Figure 2B:
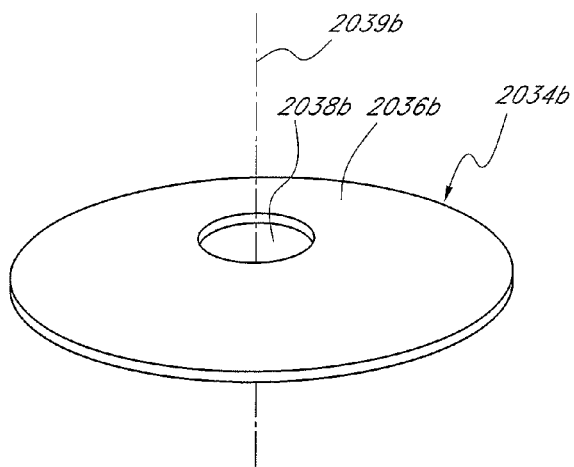
FIG. 2B is a perspective view of an embodiment of a substantially flat mask configured to increase depth of focus.

FIG. 2A illustrates one embodiment of a mask 2034a. The mask 2034a can include an annular region 2036a surrounding an aperture 2038a substantially centrally located on the mask 2034a. The aperture 2038a can be generally located around a central axis 2039a, referred to herein as the optical axis of the mask 2034a. The aperture 2038a can be in the shape of a circle. FIG. 2B illustrates another embodiment of a mask 2034b similar to the mask 2034a illustrated in FIG. 2A. The annular region 2036a of the mask 2034a of FIG. 2A has a curvature from the outer periphery to the inner periphery of the annular region 2036a, while the annular region 2036b of the mask 2034b of FIG. 2B can be substantially flat (as shown in FIG. 1B). Although the examples provided herein are generally discussed in connection with the mask 2034b, any of the examples can include the mask 2034a. In addition, a variety of variations of masks that can be positioned on or within the implant body are discussed herein, and are also described in U.S. Patent Publication No. 2012/0143325, filed Feb. 10, 2012, which is incorporated by reference herein in its entirety. Any of the teachings of this prior publication can also be applied to the devices and methods in the present disclosure.

The mask 2034b can have dimensions adapted to function with the implant body to improve a patient's vision. For example, the thickness of the mask 2034b can vary depending on the location of the mask 2034b relative to the implant body. For example, if the mask 2034b is embedded within the implant body, the mask 2034b can have a thickness greater than zero and less than the thickness of the implant body. Alternatively, if the mask is coupled to a surface of the implant body, the mask 2034b may have a thickness no greater than necessary to have the desired opacity so that the mask does not add additional thickness to the intraocular lens.

In some implementations, the mask 2034b can have a substantially constant thickness. However, in other implementations, the thickness of the mask may vary between the inner periphery (near the aperture 2038b) and the outer periphery.

In general, the thickness of the mask 2034b can be less than or equal to about 200 microns, or less than or equal to about 100 microns, but preferably between about 1 micron and about 20 microns. For example, the thickness of the mask 2034b can be within the range from about 1 micron to about 40 microns, in the range from about 5 microns to about 20 microns, or otherwise. In some embodiments, the mask 2034b can include a thickness of at least about 5 microns and/or less than or equal to about 20 microns. In some embodiments, the mask 2034b can include a thickness of at least about 5 microns and/or less than or equal to about 15 microns. In certain embodiments, the thickness can be within two microns of about 15 microns, about 10 microns, about 8 microns, about 5 microns, or otherwise. In other embodiments, however, the mask may be a bulk mask and its width may extend across much of the thickness of the lens (e.g., the width of the mask may be at least about 80 percent of the thickness of the implant body or at least about 90 percent of the thickness of the implant body).

The mask 2034b can be symmetrical, e.g., symmetrical about a mask axis 2039b. In some embodiments, the outer periphery of the mask 2034b can be circular. The mask 2034b in general can have an outer diameter of at least about 3 mm and/or less than about 6 mm. In some embodiments, the mask 2034b can be circular and can include a diameter of at least about 3 mm and/or less than or equal to about 4 mm. In some embodiments, the mask 2034b can be circular and can include a diameter within a range of 0.2 mm of about 3.2 mm.

In some embodiments, the aperture 2038b can be substantially circular and can be substantially centered in the mask 2034b. The size of the aperture 2038b can be any size that is effective to increase the depth of focus of an eye of a patient with presbyopia. In particular, the size of the aperture 2038b can be dependent on the location of the mask within the eye (e.g., distance from the retina). In some embodiments, the aperture 2038b can have a diameter of at least about 0.85 mm and/or less than or equal to about 2.2 mm. In certain embodiments, the diameter of the aperture 2038b is less than or equal to about 2 mm. In some embodiments, the diameter of the aperture 2038b is at least about 1.1 mm and/or less than or equal to about 1.6 mm. In some embodiments, the diameter of the aperture 2038b is at least about 1.3 mm and/or less than or equal to about 1.4 mm.

The aperture 2038b can transmit substantially all incident light along the mask axis 2039b. The annular region 2036b can substantially prevent transmission of incident light thereon. The aperture 2038b can be a through-hole in the annular region 2036b or a substantially light transmissive (e.g., transparent) portion thereof. The aperture 2038b of the mask 2034b can be generally defined within the outer periphery of the mask 2034b.

The annular region 2036b can at least partially prevent transmission of visible light through the mask 2034b. For example, in some embodiments, the annular region 2036b can prevent transmission of substantially all or at least a portion of the spectrum of the incident visible light. In some embodiments, the annular region 2036b can prevent transmission of substantially all visible light, e.g., radiant energy in the electromagnetic spectrum that is visible to the human eye. The annular region 2036b can substantially prevent transmission of radiant energy outside the range visible to humans in some embodiments.

Preventing transmission of light through the annular region 2036b can decrease the amount of light that reaches the retina and the fovea that would not converge at the retina and fovea to form a sharp image. As discussed above, the size of the aperture 2038b is such that the light transmitted therethrough generally converges at the retina or fovea. Accordingly, a much sharper image can be presented to the retina than would otherwise be the case without the mask 2034b.

In some embodiments, the annular region 2036b can prevent transmission of at least about 90 percent of incident light. In some embodiments, the annular region 2036b can prevent transmission of at least about 92 percent, at least about 95 percent, or at least about 98 percent of all incident light. The annular region 2036b of the mask 2034b can be substantially opaque to prevent the transmission of light.

In some embodiments, the annular region 2036b can transmit no more than about 5% of incident visible light. In some embodiments, the annular region 2036b can transmit no more than about 3 percent of incident visible light. In some embodiments, the annular region 2036b can transmit no more than about 2 percent of incident visible light. In some embodiments, at least a portion of the annular region 2036b can be opaque to more than 99 percent of the light incident thereon.

As discussed above, the annular region 2036b can prevent at least partial transmission of light without absorbing the incident light. For example, the mask 2034b can be reflective or can interact with the light in a more complex manner, as discussed in U.S. Pat. No. 6,554,424, issued Apr. 29, 2003, which is hereby incorporated by reference in its entirety.

The annular region 2036b can be at least partially opaque or can be completely opaque. The degree of opacity of the annular region 2036b can prevent at least some or substantially all light from being transmitted through the mask 2034b. Opacity of the annular region 2036b can be achieved in any of several different ways. For example, the material used to make mask 2034b can be naturally opaque. As another example, the material used to make the mask 2034b can be substantially clear, but treated with a dye or other pigmentation agent to render region 2036b substantially or completely opaque. In certain embodiments, the mask can include carbon black. In yet another example, the surface of the mask 2034b can be treated physically or chemically (such as by etching) to alter the refractive and transmissive properties of the mask 2034b and make it less transmissive to light.

In some embodiments, a photochromic material can be used as the mask or in addition to mask. Under bright light conditions, the photochromic material can darken thereby creating a mask and enhancing near vision. Under dim light conditions, the photochromic material can lighten, which allows more light to pass through to the retina. In certain embodiments, under dim light conditions, the photochromic material lightens to expose an optic of the intraocular implant. Further photochromic material details are disclosed in U.S. Patent Publication No. 2013/0268071, filed Nov. 30, 2012, which is hereby incorporated by reference in its entirety.

The mask can transition between different degrees of opacity. For example, at least a portion of the mask can transition between at least a first degree of opacity and a second degree of opacity. Further details are disclosed in U.S. application Ser. No. 13/830,889, filed Mar. 14, 2013, which is hereby incorporated by reference in its entirety.

In some embodiments, the opacity of the mask can also vary in different regions of the mask. For example, the opacity of the outer edge and/or the inner edge of the mask can be less than the central region of the mask. The opacity in different regions can transition abruptly or have a gradient transition. Additional examples of opacity transitions can be found in U.S. Pat. Nos. 5,662,706, 5,905,561 and 5,965,330, all of which are hereby incorporated by reference in their entirety.

Figure 3A:
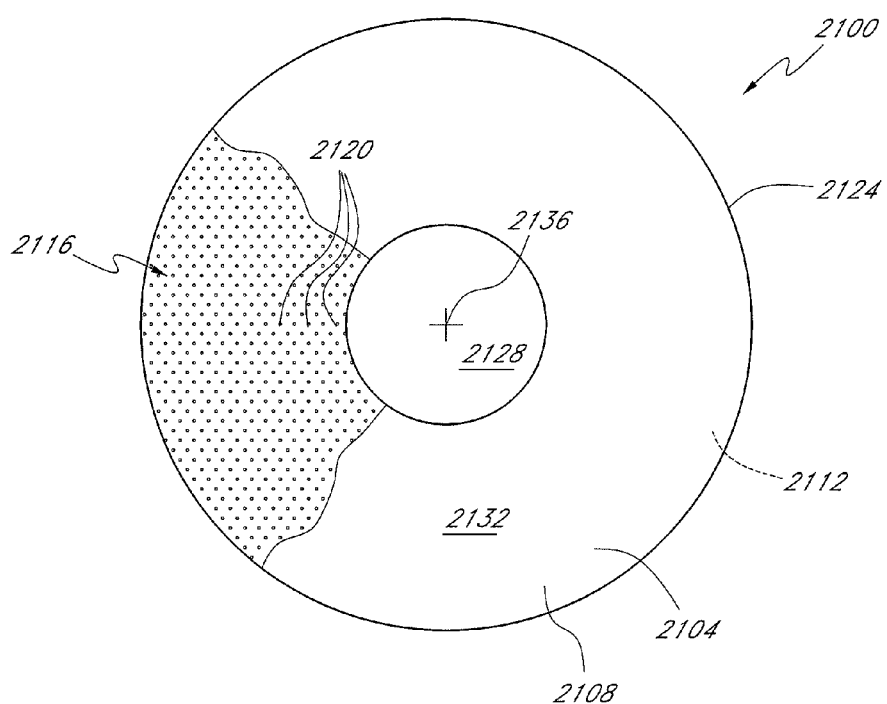
FIG. 3A is a top view of another embodiment of a mask configured to increase depth of focus.
Figure 3B:
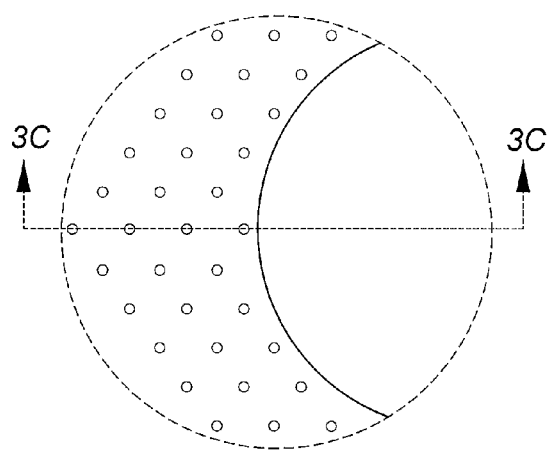
FIG. 3B is an enlarged view of a portion of the view of FIG. 3A.
Figure 3C:
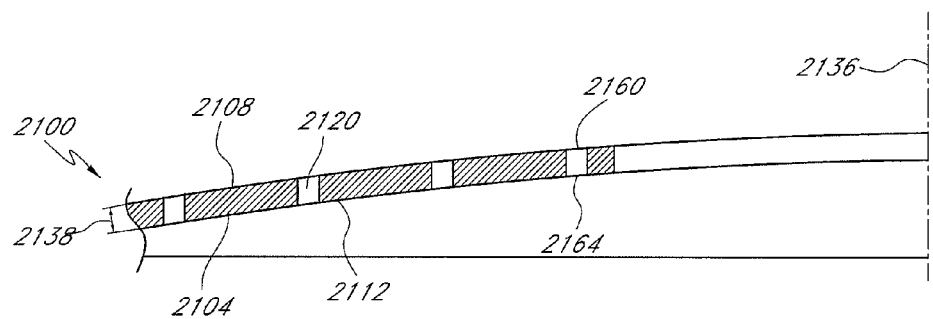
FIG. 3C is a cross-sectional view of the mask of FIG. 3B taken along line 3C-3C.

FIGS. 3A-3C show another embodiment of a mask 2100 capable of increasing depth of focus of an eye of a patient with presbyopia. The mask 2100 can be flat (as in FIG. 2B) or curved (as in FIG. 2A). The mask 2100 can be similar to the masks hereinbefore described, except as described differently below. The mask 2100 can be made of the materials discussed herein, including those discussed above. In addition, the mask 2100 can be formed by any suitable process. The mask 2100 can be applied to and/or embedded in an IOL.

The mask 2100 can include a plurality of holes 2120. When the mask 2100 is embedded in the lens body, the lens body can extend at least partially through the holes, thereby creating a bond (e.g. material "bridge") between the lens body on either side of the mask. Further disclosure regarding the material "bridge" can be found in U.S. Publication No. 2011/0040376, filed Aug. 13, 2010, which is incorporated by reference herein in its entirety.

The holes 2120 of the mask 2100 shown in FIG. 3A can be located anywhere on the mask 2100. In some embodiments, substantially all of the holes are in one or more regions of a mask. The holes 2120 of FIG. 3A extend at least partially between the anterior surface 2108 and the posterior surface 2112 of the mask 2100. In some embodiments, each of the holes 2120 includes a hole entrance 2160 and a hole exit 2164. The hole entrance 2160 is located adjacent to the anterior surface 2108 of the mask 2100. The hole exit 2164 is located adjacent to the posterior surface 2112 of the mask 2100. In some embodiments, each of the holes 2120 extends the entire distance between the anterior surface 2108 and the posterior surface 2112 of the mask 2100. Further details about possible hole patterns are described in U.S. Patent Publication No. 2012/0143325, filed Feb. 10, 2012, which is incorporated by reference herein in its entirety.

Figure 4:
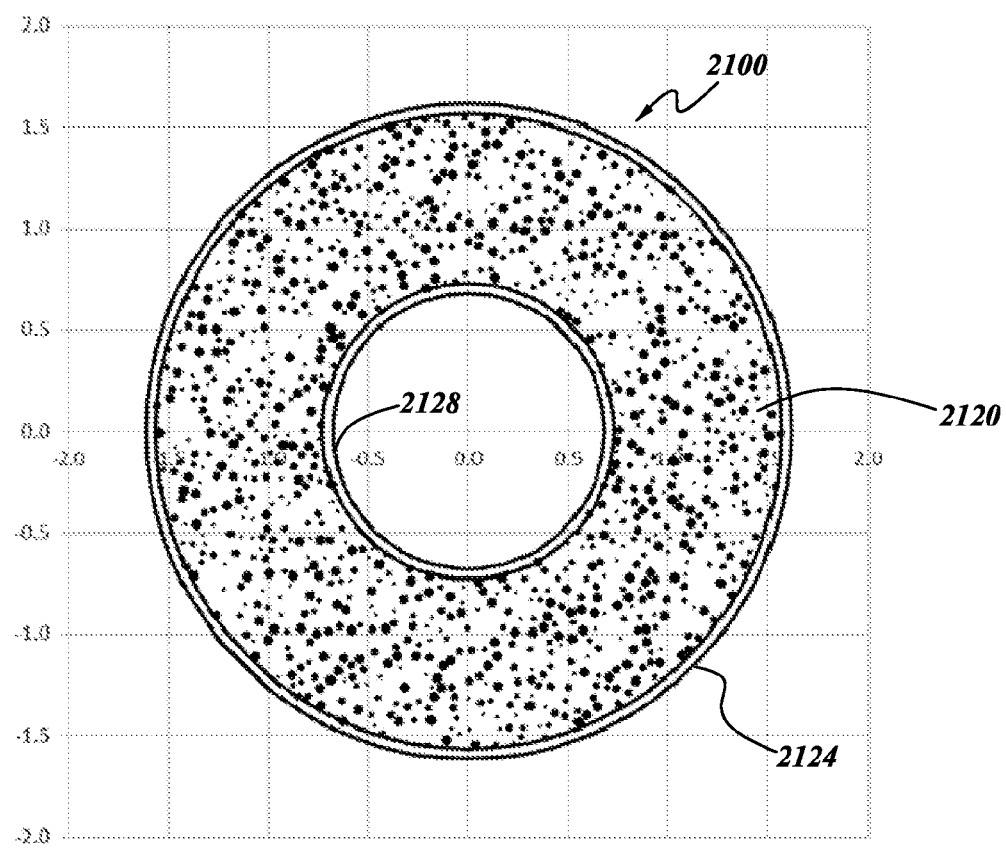
FIG. 4 is a graphical representation of one arrangement of holes of a plurality of holes that may be formed in the mask.

FIG. 4 illustrates a graphical representation of the hole pattern of the mask 2100. In some embodiments, the mask 2100 can include an annular region near the outer periphery 2124 of the mask having no holes. In certain embodiments, there are no holes within 0.1 mm of the outer periphery 2124 of the mask 2100.

The holes in the mask serve at least two purposes: the holes provide some light transmission and, as just discussed with respect to FIGS. 3A-3C, the holes create areas where the material of the implant body can extend through to create a material "bridge" that holds the mask in place. Advantageously, if the mask is in a position between the posterior and anterior surfaces of a lens body, the holes through the mask can help to prevent delamination of the interface between the mask and the lens body. Delamination can occur during manipulation of the intraocular implant such as when the intraocular implant is folded or rolled and placed into a tube to be implanted into the patient. The lens body can extend through the holes, thereby creating a bond (e.g. material "bridge") between the lens body on either side of the mask. Delamination can also be reduced by matching mechanical properties (e.g. elastic modulus) of the mask to the lens body. Another method to reduce delamination is to create a bond between the lens body and the mask. For example, the lens body and the mask can have cross-linking bonds or van der Waals forces between them.

It can be desirable to decrease or minimize the total amount of light that passes through the mask in order to increase or maximize near image contrast. Delamination can be prevented with a relatively small total area of the mask having holes for "bridges". For example, an area of about 3% of the mask can include holes which can balance increasing or maximizing mechanical strength and reducing or minimizing optical effects of the holes. In certain embodiments, the anterior surface of the mask has a mask surface area, and the light transmission structures (e.g., holes) in the mask have a total area on the anterior surface of the mask of about 1% to about 5% of the mask surface area. To limit the impact of diffraction of light passing through the holes of the mask, the holes can be made as small as possible. The Airy disc from each hole is larger the smaller the hole size, so the composite diffraction pattern produced by the pattern of holes becomes larger as well. The composite diffraction pattern spreads light over a larger portion of the retina, decreasing the local brightness of diffracted light and making diffraction artifacts less visible. Diffraction patterns produced by a pattern of holes also tends to have a chromatic component such that the diffraction halo tends to graduate in color radially. Varying the size of the holes produces this effect in multiple scales, which scrambles the color of the halo. This reduces color contrast in the halo, making it less noticeable.

The outer diameter of the outer periphery of the mask can be varied. In certain embodiments, the outer diameter is selected to selectively allow an amount of light to pass to the retina of the eye. The pupil of the eye changes size in different lighting condition. In low light situations, the pupil of the eye enlarges to let more light into the eye. The outer diameter can be selected so that light does not pass outside the outer periphery of the mask in relatively high light conditions, and so that at least some light can pass outside the outer periphery of the mask in relatively low light conditions. The pupil size of patients often can vary; therefore, the outer diameter of the mask can be selected for a specific patient pupil size. For example, for patients with relatively small pupils, dim light may present more of a vision issue than for patients with larger pupils. For smaller-pupil patients, a mask with more light transmission and/or a smaller outer diameter will increase light reaching the retina and improve vision in dim light situations. Conversely, for larger pupil patients, less light transmission and/or a larger outer diameter mask may improve low-contrast near vision and block more unfocused light. The masked IOLs of the present application give the surgeon flexibility to prescribe the appropriate combination of masked IOL features for particular patients.

In certain embodiments, the center of the aperture of the mask is off-center to the center of the lens body. By having an aperture off-center to the optical center of the lens body, the intraocular lens can be rotated during the implantation procedure so that the optical center of the patient's eye can be aligned with the center of the aperture. The vision of the patient can be improved by aligning the optical center of the patient's eye with the aperture center.

In some embodiments, the mask 2100 can include an annular region near the outer periphery 2124 of the mask having no holes. In certain embodiments, there are no holes within 0.1 mm of the outer periphery 2124 of the mask 2100.

In some embodiments, the mask can include an annular region around the inner periphery of the mask having no holes. In certain embodiments, there are no holes within 0.1 mm of the aperture 2128.

In some embodiments, the holes 2120 each have the same diameter. In certain embodiments, the holes 2120 can include one or more different diameters. In some embodiments, the diameter of any single hole 2120 is at least about 0.01 mm and/or less than or equal to about 0.02 mm. In some embodiments, the diameter of the holes 2120 can vary within 0.001 mm of one or more of the following hole diameters: 0.010 mm, 0.013 mm, 0.016 mm, and/or 0.019 mm. In some embodiments, holes of different diameters are interspersed throughout at least a portion of the mask 2100. In some embodiments, the holes are interspersed at irregular locations throughout at least a portion of the mask 2100.

In certain embodiments, the mask includes holes greater than about 7 microns in diameter (e.g., greater than a cross-sectional area of about 35 $\mu m^2$), and preferably greater than about 10 microns in diameter (e.g., greater than a cross-sectional area of about 75 $\mu m^2$). In certain embodiments, the mask includes holes greater than about 7 microns in diameter (e.g., greater than a cross-sectional area of about 35 $\mu m^2$) and less than about 20 microns in diameter (e.g., less than a cross-sectional area of about 320 $\mu m^2$). In further embodiments, the mask includes holes less than about 50 microns in diameter (e.g., less than a cross-sectional area of about 2000 $\mu m^2$. Holes with diameters less than 7 microns may not be large enough for lens material such as silicone or acrylic to enter and migrate to form a bridge. However, the viscosity of the lens material will determine whether the material will be able to migrate into the hole to form the bridge and a minimum cross-sectional area of the hole may be dependent on the material of the implant body. If the material of the implant body does not migrate into a hole, that hole may create a bubble that could interfere with the visual performance of the implant.

In a certain embodiment, the mask includes randomly or pseudo-randomly placed holes across the mask. The mask can include holes with one of four hole diameters within the parameters provided above. There can be an equal number of holes with each hole diameter. An algorithm can be used to randomly or pseudo-randomly assign the variously sized holes to locations across the mask annulus. The rules for the randomization program can include (1) that there be no "collisions" of the holes (e.g., the holes have no contact with each other), (2) that no holes interfere with the inner and outer peripheral edges of the mask, and (3) that the holes are placed in such a way as to create substantial uniform density across the mask annulus. For example, the rules for the randomization program may include one or more of these rules.

In some embodiments there are at least about 1000 holes and/or less than or equal to about 2000 holes. In some embodiments, there are at least about 1000 holes and/or less than or equal to about 1100 holes. In some embodiments, the number of holes is within ten holes of about 1040 holes. In some embodiments, there are an equal number of holes of each diameter. In some embodiments, the number of holes having each diameter is different.

In some embodiments, the holes are interspersed at irregular locations throughout at least a portion of the mask 2100. In some embodiments, holes of different diameters are evenly interspersed throughout at least a portion of the mask 2100. For example, the mask 2100 can include a plurality of non-overlapping hole regions. The sum of the surface area of the plurality of non-overlapping hole regions can equal the total surface area of the entire hole region of the mask. In some implementations, each region of the plurality of regions can include a number of holes, each of the holes having a different diameter. In some implementations, the number of holes in each region can equal the number of different hole sizes in the entire hole region. In some implementations, an amount of open area within each hole region can be substantially the same. In some implementations, each hole region can include the same number of holes.

Any of the masks discussed herein can be formed of any suitable material, including, but not limited to, at least one of an open cell foam material, an expanded solid material, and/or a substantially opaque material. In some embodiments, the material used to form the mask can have relatively high water content. In some embodiments, the materials that can be used to form the body 2104 include polymers (e.g. PMMA, PVDF, polypropylene, polycarbonate, PEEK, polyethylene, polystyrene, PVC, polysulfone), hydrogels, metals, metal alloys, or carbon (e.g., graphene, pure carbon), but preferably acrylic copolymers or silicone.

In some embodiments, the durometer (type A) of the mask material can be less than or equal to about 100, for example, between about 25 and about 50, such as about 40. In some embodiments, the percent elongation to break for the mask material can be between about 150 percent and about 600 percent, for example, within about 50 percent of each of about 200 percent, 250 percent, 300 percent, 350 percent, 400 percent, 450 percent, 500 percent, or about 550 percent. In some instances, the elongation can be between about 150 percent and about 200 percent, such as about 175 percent. In some instances, the elongation can be between about 500 percent and about 600 percent, such as about 550 percent. In some embodiments, the tensile strength of the mask material can be less than or equal to 15 MPa, for example, within about 2 MPa of each of about 10 MPa, 8 MPa, 6 MPa, or 4 MPa. In some embodiments, the modulus of elasticity of the mask material can be between about 0.5 MPa and about 2 MPa, for example, within about 0.25 MPa of about 0.75 MPa, 1.0 MPa, 1.25 MPa, 1.5 MPa, or 1.75 MPa.

As described above, methods of manufacturing the IOL and methods of implanting the IOL can degrade optical performance of the IOL if the material properties of the IOL and the mask are not compatibly selected to withstand, for example, deformations (such as those resulting from swelling that may occur during chemical extractions or treatments), and temperature shifts. As such, it can be desirable to select a mask material and a lens material having appropriate material properties to allow the device to revert to, or otherwise achieve, a desired optical performance even after suffering some type of deformation or temperature differential.

In some implementations, the modulus of elasticity of the mask material can be within about 50 percent of the modulus of elasticity of the lens material. In some implementations, the modulus of elasticity of the mask material can be within about 45 percent of the modulus of elasticity of the lens material, or within about 30 percent of the modulus of elasticity of the lens material, or within about 20 percent of the modulus of elasticity of the lens material, or within about 10 percent of the modulus of elasticity of the lens material, or within about 5 percent of the modulus of elasticity of the lens material. In some implementations, the modulus of elasticity of the mask material can be greater than or equal to the modulus of elasticity of the lens material; while, in other implementations, the modulus of elasticity of the mask material can be less than the modulus of elasticity of the lens material. In some implementations, the modulus of elasticity of the mask material can be substantially the same as the modulus of elasticity of the lens material.

Since the lens material is more voluminous than the mask material, the properties of the lens material will generally dominate. Thus, it can be particularly advantageous if the elasticity of the mask material is at least as great as that of the lens material in order to allow the embedded mask to react to deformation of the lens without becoming damaged or displaced.

In some implementations, the mask material can be the same as the lens material. In some implementations, the mask material can include a hydrophilic or hydrophobic material. In some implementations, the mask material can include an acrylic copolymer or silicone.

In some embodiments, the lens material can include a hydrophilic or hydrophobic material. In some implementations, the lens material can include an acrylic copolymer or silicone. The modulus of elasticity of the lens material can be between about 0.50 MPa and about 1.5 MPa, for example, between about 0.75 MPa and about 1.25 MPa, such as within about 0.1 MPa of each of about 1.0 MPa, 1.1 MPa, 1.2 MPa, or 1.3 MPa. The percentage of elongation to break can be between about 150 percent and about 200 percent, for example, between about 160 percent and about 190 percent or between about 170 percent and about 180 percent, such as about 175 percent.

In some implementations, the coefficient of thermal expansion of the mask material is substantially similar to that of the lens material. In this way, the mask material and the lens material respond to temperature differentials in similar ways to avoid the development of stress or strain between the mask and the IOL. In some implementations, the coefficient of thermal expansion of the mask material can be within about 30 percent of the coefficient of thermal expansion of the lens material, or within about 20 percent of the coefficient of thermal expansion of the lens material, or within about 10 percent of the coefficient of thermal expansion of the lens material, or within about 5 percent of the coefficient of thermal expansion of the lens material. In some implementations, the coefficient of thermal expansion of the mask material can be substantially the same as the coefficient of thermal expansion of the lens material.

In some implementations, the mask material can be the same as the lens material. In some implementations, the mask material can include a hydrophilic or hydrophobic material. In some implementations, the mask material can include an acrylic copolymer or silicone.

In some implementations, the lens material can include a hydrophilic or hydrophobic material. In some implementations, the mask material can include an acrylic copolymer or silicone.

Methods of Use

Any of the IOLs described herein can be implanted using an injection system. The method can include injecting the IOL through a small cartridge tip having an inside diameter of less than or equal to about 2.0 mm, for example, within about 0.2 mm of about 1.5 mm, preferably less than or equal to about 1.5 mm, such as between about 1.5 mm and about 1.25 mm or between about 1.25 mm and about 1.0 mm. The injection system can deliver the IOL through an incision having a chord length of less than or equal to about 2.4 mm. The IOL can be configured to transition between a pre-injection configuration (e.g., rolled up for implantation) and a post-injection configuration (expanded, in-situ shape). The pre-injection configuration can be substantially smaller than the post-injection configuration.

In some implementations, it can be desirable for the IOL to transition between the pre-injection configuration and the post-configuration without substantially changing optical performance. For example, the optical power of the IOL prior to injection can be within about 0.5 diopters, preferably within about 0.3 diopters, or within about 0.2 diopters, or within about 0.1 diopters, of the optical power of the IOL after injection.

As mentioned above, the IOL can expand when it is introduced into the body because of the difference between room and body temperature in the eye, e.g., in an anterior chamber of the eye. In some implementations, the temperature differential can be between about 5° C. and about 20° C., for example, between about 5° C. and about 10° C., between about 10° C. and about 15° C., or between about 15° C. and about 20° C. The room temperature can be between about 18° C. and about 26° C., and the temperature of the anterior chamber of the eye can be between about 18° C. (e.g., transiently during irrigation/aspiration) and about 37° C.

In some implementations, it can be desirable for the IOL to undergo the temperature differential without substantially changing optical performance. For example, the optical power of the IOL at room temperature can be within about 0.15 diopters, such as within about 0.03 diopters of about 0.1 diopters, for example, about 0.13 diopters, of the optical power of the IOL at body temperature.

Methods of Manufacturing

Various techniques can be used for forming the mask. In some embodiments, the mask can be formed using a mask material alone or in combination with an opacification agent. The mask material can include any of the mask materials described herein, for example, silicone or an acrylic copolymer. In some implementations, the mask material can be combined with an opacification agent, such as carbon black, or any class 3 medical device material.

In some embodiments, the resulting mixture can be used to form a mask film having a thickness equal to the desired mask thickness. Techniques for forming the mask film can include allowing mask material to spread to a desired thickness by gravity or by spinning. Each mask can then be formed from the mask film using a stamp, sieve, die, laser, or other machine. In an alternative technique, the mask material can be formed into a tube (e.g., using an extrusion process), and masks having the desired thickness can be cut from the tube. Further mask materials and methods of making a mask are disclosed in U.S. Pub. No. 2011/0040376, filed Aug. 13, 2010, which is incorporated by reference herein in its entirety.

After forming the mask, the mask can be embedded within or applied to a lens body. For example, the method can include pre-dosing a first lens forming mold portion with a first amount of lens material and positioning the mask on a positioning mold portion. Thereafter, the first lens forming mold portion and the positioning mold portion can be joined together, and the lens material can be at least partially cured. After partially curing the lens material, at least the first lens forming mold portion can be cooled to facilitate the separation of the mold portions without disrupting the position of the mask. Once the mold portions are separated, a second amount of lens material can be added to the first lens forming mold portion and/or a second lens forming mold portion, and the first lens forming mold portion and the second lens forming mold portion can be joined together. In this configuration, the first and second amounts of lens material can be at least partially cured, for example, using a light cure. Finally, the final curing process can be carried out using thermal curing. In some implementations, depending on the mask and lens materials, the IOL can undergo chemical extraction to remove any impurities. Further details regarding this manufacturing method or alternatives can be found in U.S. patent application Ser. No. 13/830,889 and U.S. Publication No. 2014/0131905, both filed Mar. 14, 2013, which are incorporated by reference herein in their entireties.

Alternatively, the intraocular lens can be manufactured using stereolithography to image the mask within the lens. The method can include providing a first amount of photoreactive lens material. Next, the method can also include forming a first layer of the intraocular lens by curing the first amount of photoreactive lens material to form the desired shape. Thereafter, the method can include providing a second amount of photoreactive lens material over the cured first layer and forming a second layer of the intraocular lens by curing the second amount of photoreactive lens material to form the desired shape. This process can be repeated to additively form the lens. After one or more initial layers of the lens have been formed, a mask can be imaged within the initial layers by activating dyes such as those described in U.S. Publication No. 2013/0268071, filed Nov. 30, 2012, and U.S. Pat. No. 8,604,098, filed Jul. 6, 2011, which are incorporated by reference herein in their entireties, by laser ablation, or by other methods to create opacity, as described in U.S. Publication 2013/0289543, filed Mar. 12, 2013, which is also by incorporated by reference herein in its entirety. Once the mask is in place, the process of providing and curing layers of photoreactive lens material can be continued such that the mask is embedded within the completed lens. The lens can be formed such that the mask can be imaged within the lens in a manner that provides the mask with the same physical properties as the lens, thus allowing the mask to flex with the lens without damage.

As explained above, the manufacturing method can include an extraction process to remove impurities. For example, the method can include a chemical extraction process. During the chemical extraction process, the IOL can undergo a volumetric increase of at least about 5%, sometimes at least about 10%.

In some implementations, it can be desirable to subject the IOL to the chemical extraction process without substantially changing optical performance. For example, the optical power of the IOL before extraction can be within about 0.5 diopters, preferably within about 0.3 diopters, or within about 0.2 diopters, or within about 0.1 diopters, of the optical power of the IOL after extraction.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although certain embodiments and examples have been described herein, it will be understood by those skilled in the art that many aspects of the methods and IOLs shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. An intraocular lens comprising:
    an elastic lens body comprising lens material, the lens body being flexible enough to be injected through an incision less than 3.5 mm; and
    an elastic mask with an aperture for improving depth of focus, the mask comprising an opacification agent and a mask material, the mask material being different from the lens material, the mask material being flexible and having a modulus of elasticity that is sufficiently matched with a modulus of elasticity of the lens material to reduce delamination between the mask and lens body.

2. The intraocular lens of claim 1, wherein the mask material comprises silicone.

3. The intraocular lens of claim 1, wherein the mask material comprises acrylic.

4. The intraocular lens of claim 1, wherein the mask comprises a plurality of holes characterized in that at least one characteristic selected from the group consisting of a hole size, hole shape, hole orientation, and hole spacing of the plurality of holes is varied to reduce the tendency of the holes to produce visible diffraction patterns.

5. The intraocular lens of claim 1, wherein the mask comprises a thickness of less than or equal to about 200 microns.

6. The intraocular lens of claim 1, wherein the lens body has an outer diameter between about 5 mm and about 6 mm.

7. The intraocular lens of claim 1, wherein the mask is embedded entirely between a posterior surface and an anterior surface of the lens body.

8. A method of manufacturing an intraocular lens, the method comprising:
   forming a mask with an aperture for improving depth of focus from a mask material;
   inserting a lens material into a mold; and
   curing the lens material to form a lens body, the lens body comprising the mask therein wherein the lens body is flexible enough to be injected through an incision less than 3.5 mm; the mask comprising an opacification agent and the mask material, the mask material being different from the lens material, the mask material being flexible and having a modulus of elasticity that is sufficiently matched with a modulus of elasticity of the lens material to reduce delamination between the mask and the lens body.

9. The method of claim 8, wherein forming the mask comprises forming a plurality of holes within a mask body, characterized in that at least one characteristic selected from the group consisting of a hole size, hole shape, hole orientation, and hole spacing of the plurality of holes is varied to reduce the tendency of the holes to produce visible diffraction patterns.

10. The intraocular lens of claim 1, wherein mask material comprises a polymer.

11. The intraocular lens of claim 1, wherein the mask material comprises a highly fluorinated polymer.

12. The intraocular lens of claim 1, wherein the mask material comprises polyvinylidene fluoride.

* * * * *